(12) United States Patent
Sadhu

(10) Patent No.: US 10,101,795 B2
(45) Date of Patent: Oct. 16, 2018

(54) SYSTEM-ON-CHIP (SOC) AND METHOD FOR DYNAMICALLY OPTIMIZING POWER CONSUMPTION IN THE SOC

(71) Applicant: Wipro Limited, Bangalore (IN)

(72) Inventor: Radha Krishna Moorthy Sadhu, Bangalore (IN)

(73) Assignee: Wipro Limited, Bangalore (IN)

( * ) Notice: Subject to any disclaimer, the term of this patent is extended or adjusted under 35 U.S.C. 154(b) by 133 days.

(21) Appl. No.: 14/981,708

(22) Filed: Dec. 28, 2015

(65) Prior Publication Data

US 2017/0131755 A1 May 11, 2017

(30) Foreign Application Priority Data

Nov. 10, 2015 (IN) .......................... 6075/CHE/2015

(51) Int. Cl.
*G06F 1/32* (2006.01)
*G06F 13/26* (2006.01)
*G06F 13/40* (2006.01)
*G06F 13/42* (2006.01)
*G06F 15/78* (2006.01)
*G06F 19/00* (2018.01)
*G16H 10/20* (2018.01)

(52) U.S. Cl.
CPC .............. *G06F 1/324* (2013.01); *G06F 1/325* (2013.01); *G06F 13/26* (2013.01); *G06F 13/4022* (2013.01); *G06F 13/4291* (2013.01); *G06F 15/7807* (2013.01); *G06F 19/00* (2013.01); *G06F 19/3456* (2013.01); *G16H 10/20* (2018.01); *Y02D 10/126* (2018.01); *Y02D 10/151* (2018.01)

(58) Field of Classification Search
CPC combination set(s) only.
See application file for complete search history.

(56) References Cited

U.S. PATENT DOCUMENTS

| | | | | |
|---|---|---|---|---|
| 5,163,146 A | * | 11/1992 | Antanaitis, Jr. | ........... G06F 1/08 713/501 |
| 5,392,435 A | * | 2/1995 | Masui | ................... G06F 1/3215 710/260 |
| 5,659,759 A | * | 8/1997 | Yamada | .................. G06F 13/26 710/262 |
| 5,894,577 A | * | 4/1999 | MacDonald | .......... G06F 1/3215 710/260 |
| 6,115,823 A | | 9/2000 | Velasco et al. | |
| 7,093,153 B1 | * | 8/2006 | Witek | ....................... G06F 1/08 713/600 |
| 7,219,245 B1 | | 5/2007 | Raghuvanshi | |
| 8,117,475 B2 | | 2/2012 | Pesavento et al. | |

(Continued)

*Primary Examiner* — Eric T Oberly
(74) *Attorney, Agent, or Firm* — LeClairRyan PLLC

(57) ABSTRACT

The present disclosure relates to a method for dynamically optimizing power consumption in a System-on-Chip (SoC). The method comprises receiving at least one interrupt signal from a peripheral controller. The method further comprises switching clock frequency of the peripheral controller to a lower clock frequency than a normal operating clock frequency upon receiving the at least one interrupt. The method further comprises providing the lower clock frequency than the normal operating clock frequency to the peripheral controller for dynamically optimizing the power consumption of the SoC.

7 Claims, 2 Drawing Sheets

(56) References Cited

U.S. PATENT DOCUMENTS

2002/0042856 A1\* 4/2002 Hartwell .................. G06F 13/24
710/263
2004/0205371 A1 10/2004 Huang
2007/0038829 A1\* 2/2007 Tousek ................ G06F 13/1663
711/167
2011/0258469 A1\* 10/2011 Guan .................... G06F 1/3203
713/320

\* cited by examiner

SYSTEM-ON-CHIP (SOC) AND METHOD FOR DYNAMICALLY OPTIMIZING POWER CONSUMPTION IN THE SOC

This application claims the benefit of Indian Patent Application Serial No. 6075/CHE/2015 filed Nov. 10, 2015, which is hereby incorporated by reference in its entirety.

FIELD OF THE DISCLOSURE

The present subject matter is related, in general, to power management in an Integrated Circuit (IC), more particularly, to reduce power consumption in a System-on-Chip (SoC). The subject matter discloses a method for dynamically optimizing power consumption in the SoC by reducing clock frequencies to a peripheral controller in the SoC.

BACKGROUND

System-on-Chip integrated circuits are becoming ever more popular in various applications including embedded applications in one or more devices such as set-top-boxes, mobile phones, portable media devices, Personal Digital Assistant (PDA), computers and so on. The SoC is configured with Central Processing Unit (CPU), memory unit, peripheral controllers corresponding to one or more peripherals connected to the one or more devices, bus interfaces and other units which are presently configurable in the SoCs. The peripheral controllers operate the peripherals connected to the SoC. For example, a display controller operates functionality of a display unit and a keyboard controller operates functionality of a keyboard. Further, the peripherals perform various operations like data input/output and/or data storage. These peripheral controllers are operated by the CPU. The peripheral controllers are operated based on clock frequencies provided from a clock controller connected to the CPU and each of the peripheral controllers. Usually, each peripheral controller may generate interrupts to the CPU. The CPU intervention is provided to the interrupts i.e. the CPU services the interrupts. Presently, the CPU services the interrupts based on priority of the interrupts. The priority of the interrupts is set by using an interrupt controller which is connected between each of the peripheral controllers and the CPU. The interrupt controller prioritizes the interrupts received from the peripheral controller and set the interrupts like a precautionary interrupt or interrupts like data transfer completion of a low speed peripheral to low priority. In cases when the peripheral controllers issue the interrupts, the peripheral controller goes to a wait state waiting for the interrupts to be processed by the CPU. At such a stage, the clock controller provides the clock frequencies with the same rate to the peripheral controllers. As a result of such operation, power is consumed for the peripheral controller. For example, in normal scenario, the high priority interrupts are processed first than the low priority interrupts. While the interrupts from peripheral which are prioritized as low are not being processed, peripheral controller is waiting for the CPU to take action on such interrupts. At such a stage, the clock power is consumed as normal peripheral operation since same clock frequency is provided to the peripheral. In such a case, power consumed during this waiting period is same as normal peripheral operation. For example, in a typical complex SoC designs, there could be few hundreds of interrupts that needs CPU intervention. Hence, to process a low priority interrupt it might take up to few milliseconds. During such period, the peripheral controller, which generated low priority interrupt, is waiting for the CPU intervention and clock frequency given to the peripheral controller is running at full speed. As an example, consider a Serial Peripheral Interfaces (SPI) peripheral which is in a master mode. Upon receiving requested data for reading or writing, the SPI peripheral issues the interrupts and waits for the CPU to take an action. If the CPU is busy with other tasks, the clock frequency given by the clock controller to the SPI is still running in full speed even the SPI peripheral is in the wait state i.e. the SPI peripheral is not performing any task during such period. At such a stage, dynamic power is consumed by the clock controller (clock tree build from a clock source) to the peripheral and at the peripheral controllers (flops) in the SoC. There is necessary to reduce the power consumption of the SoC.

In one conventional method, the power consumption is reduced by reducing the clock frequencies to the peripheral controllers by reducing the clock frequencies or turning off the clock controller dynamically when feasible. However, such slowing down the clock frequencies or turning off the clock controller is achieved upon receiving instructions from the CPU. Particularly, the CPU first determines the type of the interrupts needs to be processed. Then, the CPU intimates the clock controller to slow down the clock frequencies or turn off the clock controller as per the type of the interrupts. Such a way of determining the type of the interrupts and then intimating to the clock controller is very time consuming and may result in long wait period for the clock controller and/or the peripheral controllers and needs additional software code and may be additional logic to indicate the peripheral state.

In one conventional method, a power management logic is implemented which firstly determines state of the peripheral controllers based on events generated by the peripheral controllers. When the events indicate that a peripheral controller has a lack of activity for a given period of time, a request is sent to the peripheral controller by the power management logic to enter into a power saving state. The peripheral controller then responds by sending an acknowledge signal. This handshaking is typically necessary to avoid uncompleted, pending transfers or tasks (e.g., pending FIFO or bus transfers). When the power management logic receives the acknowledge signal, indicating that the peripheral controller is ready to go into a power reduction state, the power management logic gates off or slows down the clock provided to the peripheral controller. However, such a way of determining the state of the peripheral controller and then reducing the clock frequencies is time consuming and needs additional power management logic built in the peripheral controller logic.

SUMMARY

One or more shortcomings of the prior art are overcome and additional advantages are provided through the present disclosure. Additional features and advantages are realized through the techniques of the present disclosure. Other embodiments and aspects of the disclosure are described in detail herein and are considered a part of the claimed disclosure.

In one embodiment, the present disclosure relates to a method for dynamically optimizing power consumption in a System-on-Chip (SoC). The method comprises receiving at least one interrupt signal from a peripheral controller. The method further comprises switching clock frequency of the peripheral controller to a lower clock frequency than a normal operating clock frequency upon receiving the at least one interrupt. The method further comprises providing the lower clock frequency than the normal operating clock frequency to the peripheral controller for dynamically optimizing the power consumption of the SoC.

In another embodiment, the present disclosure relates to a System-on-Chip (SoC) with dynamically optimizing power consumption. The SoC comprises a processing unit, a memory communicatively coupled to the processing unit, one or more peripheral controllers and a clock control unit. The memory stores processor/controller-executable instructions, which, on execution, cause the processing unit to process at least one interrupt signal. The one or more peripheral controllers provide the at least one interrupt signal to the processing unit for processing the at least one interrupt signal. The clock control unit is configured to receive the at least one interrupt signal from a peripheral controller of the one or more peripheral controllers. The clock control unit is further configured to switch clock frequency of the peripheral controller to a lower clock frequency than a normal operating clock frequency upon receiving the at least one interrupt signal. The clock control unit is further configured to provide the lower clock frequency than the normal operating clock frequency to the peripheral controller for dynamically optimizing the power consumption of the SoC.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

Figure 1:
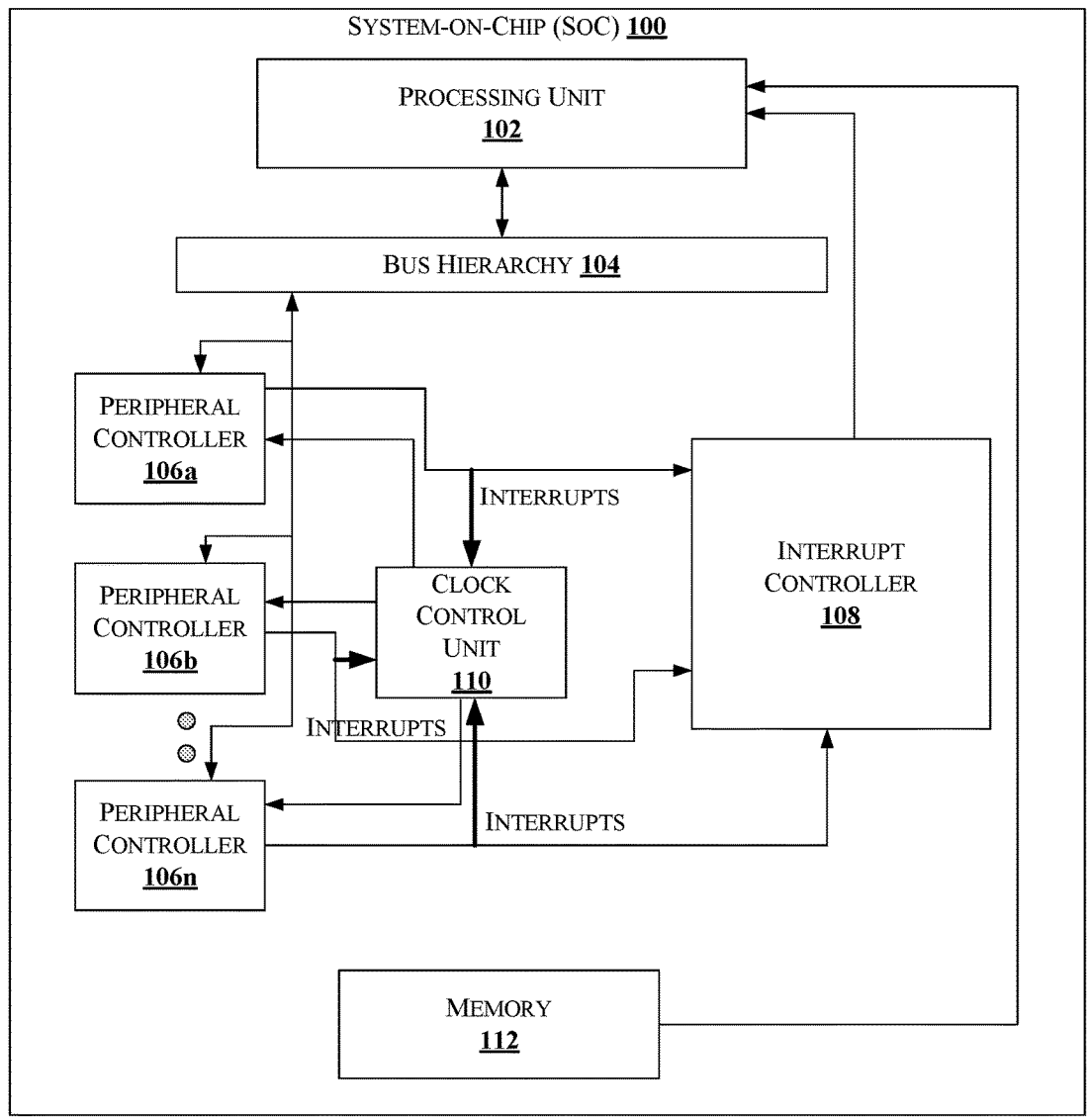
FIG. 1 illustrates an exemplary System-on-Chip (SoC) whose power consumption is optimized by reducing clock frequencies to peripheral controllers in wait state in accordance with some embodiments of the present disclosure.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented executed by a processor or controller, whether or not such processor or controller is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

The present disclosure relates to a method and a System-on-Chip (SoC) for dynamically optimizing power consumption in the SoC. Particularly, normal operating clock frequency provided to a peripheral controller in the SoC is reduced to a lower clock frequency. The normal operating clock frequency is reduced to the lower clock frequency when there is a wait period or data rate adjustment involved due to interrupts like low priority or precautionary interrupt for being serviced by a Central Processing Unit (CPU) of the SoC. In an embodiment, the normal operating clock frequency refers to the frequency required for normal operation of the peripheral controllers without impacting any performance of the peripheral. After the interrupts are serviced by the CPU, the peripheral controller operates with the normal operating clock frequency not impacting performance of the peripheral controller. In such a way, during the wait state or the wait period of the peripheral controller, the normal operating clock frequency is reduced to the lower clock frequency. Thus, the power consumption of the SoC is reduced i.e. the power consumed by clock control unit (clock tree build) and the peripheral controller (peripheral flops) is reduced during the wait state of the peripheral controller without impacting the peripheral performance as the frequency is reduced during the wait period. For example, power consumption is reduced when a data reception interrupt is generated by the peripheral controller (like SPI controller) for CPU intervention and clock to peripheral controller is reduced while peripheral is waiting for this CPU intervention. Another example for precautionary interrupts is, generation of an interrupt such as First-In-First-Out (FIFO) FULL-FIFO FULL from the peripheral controller (such as media storage unit) is avoided because of the precautionary interrupts like ALMOST FULL provided to the clock control unit. This would enable switching data path clock or peripheral controller clock to a lower frequency using glitch free clock muxes in the clock control unit of the SoC. Such a way, rate at which the data is pumped in to the peripheral controller is controlled and the occurrence of FIFO FULL or OVERFLOW is delayed or avoided. In such a case, the CPU need not process such interrupts which saves the CPU execution time and clock frequency is also reduced which saves the power consumption of the SoC. The performance of the peripheral controller is not impacted since reduction in the rate of clock frequency is achieved which does not require CPU intervention for such interrupts.

For example, normal operating clock frequency for SPI is typically 50 Mega Hertz (MHz) which can be reduced to 25 MHz on receiving of the ALMOST FULL interrupts.

FIG. 1 shows an exemplary System-on-Chip (SoC) 100 whose dynamic power consumption is optimized by reducing clock frequency to one or more peripheral controllers 106a, 106b, . . . , 106n (collectively referred to 106). When one or more peripheral controllers 106 issue one or more interrupts to the interrupt controller 108 the same interrupt is also provided to the clock control unit 110. In an embodiment, the clock control unit 110 reduces the clock frequency provided to the one or more peripheral controllers 106 which generated the interrupt. This is maintained until the processing unit 102 services the interrupt. In such a way, processing time and energy required for processing the one or more interrupts are saved which saves the power consumption as well.

In an embodiment, the SoC 100 is an Integrated Circuit (IC) which integrates all components of a device into a single chip. In an embodiment, the device includes, but is not limited to, computer and/or other electronic devices. In an embodiment, any digital circuits like Complementary Metal Oxide Semiconductor (CMOS) digital circuits, Serial Peripheral Interface (SPI), Inter Integrated Circuits (I2C) etc. having interrupts been processed by a corresponding processing unit may be considered in the present disclosure whose power consumption is optimized. Typically, the SoC 100 comprises a processing unit 102, a bus hierarchy 104, the one or more peripheral controllers 106, an interrupt controller 108 and a clock control unit 110. In an embodiment, the SoC 100 also comprises a memory 112. The details of each component contained in the SoC 100 pertaining to understanding of the disclosure are explained in below descriptions.

The processing unit 102 processes instructions which are stored in the memory 112 that enables functioning of the device. The functioning of the device may include, without limitations, operations to be performed by the device, data storage in the memory, data input and data output into and/or from the memory etc. In an embodiment, the functioning of the device is performed for corresponding one or more peripheral controllers 106 as well. For example, data storage may be performed by the processing unit 102 into a peripheral controller 106a and data may be retrieved from a peripheral controller 106b etc. and other functionalities as well which are typically performed in any SoCs. In an embodiment, the processing unit 102 is configured to process the one or more interrupts issued by the one or more peripheral controllers 106. Particularly, the processing unit 102 process and/or provides its intervention to the one or more interrupts issued by the one or more peripheral controllers 106 based on settings from the interrupt controller 108.

The bus hierarchy 104 connects each component in the SoC 100. That is, the interconnection between the processing unit 102 with the one or more peripheral controllers 106 and the interrupt controller 108 are provided through the bus hierarchy 104.

The one or more peripheral controllers 106 include, but are not limited to, controllers of various peripherals connected to the device containing the SoC 100, which are operated by the processing unit 102. The one or more peripheral controllers 106 include, without limitation, a display controller corresponding to a display unit (not shown) connected to the device, a keyboard controller corresponding to a keyboard connected to the device, a mouse controller of a mouse connected to the device, a pointing device controller corresponding to a pointing device, a media storage controller of one or more media storage component in the device, etc. In an embodiment, the one or more peripheral controllers 106 may be considered as processing Intelligent Peripherals (IP). Typically, each of the peripheral controllers 106 comprises main control logic and interface control logic depending on which each of the peripheral controllers 106 receives the clock frequency. Typically, the one or more peripheral controllers 106 issue the one or more interrupt signal just like in the existing art. In one example, the one or more peripheral controllers 106 may issue precautionary interrupt signal and/or other interrupts. The precautionary interrupt signal may relate to "ALMOST FULL" interrupt. The other interrupts may include, without limitations, peripheral interrupts which are operation based interrupt etc. In an embodiment, the one or more interrupt signal issued by the one or more peripheral controllers 106 is transmitted to the processing unit 102 for processing the one or more interrupt signal and to the clock control unit 110 based on which the clock frequency to the one or more peripheral controllers 106 is reduced. Particularly, the one or more peripheral controllers 106 goes to the wait state waiting for the processing unit 102 to process the one or more interrupt signal being issued. During the wait state of the one or more peripheral controllers 106, continuous clock frequency is still provided to the one or more peripheral controllers 106 which results in high power consumption of the SoC 100. In order to reduce and/or optimize the power consumption, the one or more interrupt signals are routed to the clock control unit 110 which is not performed in the existing art. Such routing of the one or more interrupt signal to the clock control unit 110 saves time and energy of the processing unit 102 for processing the one or more interrupt signals. This is because, sometimes the precautionary interrupt signals may take long duration and/or may not be processed at all or may be masked by the processing unit 102. In such a case, there is necessity to save the power consumption of the SoC which is usually wasted by providing continuous clock frequency to the one or more peripheral controllers 106 issuing the precautionary interrupt signal. Further, in such a way, data movement is controllable using such clock frequency reduction during "ALMOST FULL" interrupt. Additionally, in some scenarios, low priority interrupt signal may be processing after very long duration. Therefore, the clock control unit 110 reduces the clock frequencies to the one or more peripheral controllers 106 during the wait state of the one or more peripheral controllers 106 based on the received one or more interrupt signals. This results in power saving. In an embodiment, each of the peripheral controllers 106 is preconfigured to be issuing particular kind of interrupt signal as part of normal operation.

The interrupt controller 108 is a component which prioritizes and/or sets the sequence with which the one or more interrupt signal must be processed by the processing unit 102. The interrupt controller 108 may prioritize the one or more interrupt signal with high priority and low priority. Usually, the high prioritized interrupt signal is processed faster by the processing unit 102 and then the low interrupt signal is processed by the processing unit 102. In an embodiment, each peripheral controller 106 is preconfigured with priorities for interrupts. Further, particular peripheral controller issues particular interrupt signals as per the design. For example, the media storage controller is preconfigured to be issuing the precautionary interrupt signal, the keyboard controller is preconfigured to be issuing low priority interrupt signal and the display controller is preconfigured to be issuing the high priority interrupt signal.

The clock control unit 110 provides normal operating clock frequency to the one or more peripheral controllers 106 for normal functioning of the one or more peripheral controllers 106. In an embodiment, the clock control unit 110 receives the one or more interrupt signal from the one or more peripheral controllers 106 when the one or more interrupt signal are generated for processing by the processing unit 102. The one or more interrupt signal are received by the processing unit 102 after being set or prioritized by the interrupt controller 108. Then, according to the one or more interrupt signal, the clock control unit 110 reduces the normal operating clock frequency to a lower clock frequency than the normal operating clock frequency to the one or more peripheral controllers 106. In an embodiment, the clock control unit 110 reduces the normal operating clock frequency to the lower clock frequency upon receiving the precautionary interrupt signal and/or the low priority interrupt signal. In an embodiment, the clock control unit 110 may be configured with one or more Phase Locked Loops (PLLs) which provides the clock frequencies i.e. the normal operating clock frequency and/or the lower clock frequency to the one or more peripheral controllers 106. In an embodiment, the clock control unit 110 is configured with clock multiplexing logics for controlling the clock frequencies to the one or more peripheral controllers 106. In one implementation, clock rate with which the clock frequency must be provided is preconfigured to the corresponding one or more peripheral controllers 106. Particularly, clock rate for the normal operating clock frequency and/or the lower clock frequency is preconfigured. Thus, the clock control unit 110 provides the clock frequency to the corresponding one or more peripheral controllers 106 as per the preconfigured clock rate by dynamically switching between the two based on the one or more interrupt provided to the clock control unit 110.

The memory 112 stores instructions which are executable by the processor unit 102. The memory 112 stores the interrupt processing functions for one or more interrupt signal to be issued by the one or more peripheral controllers 106.

Figure 2:
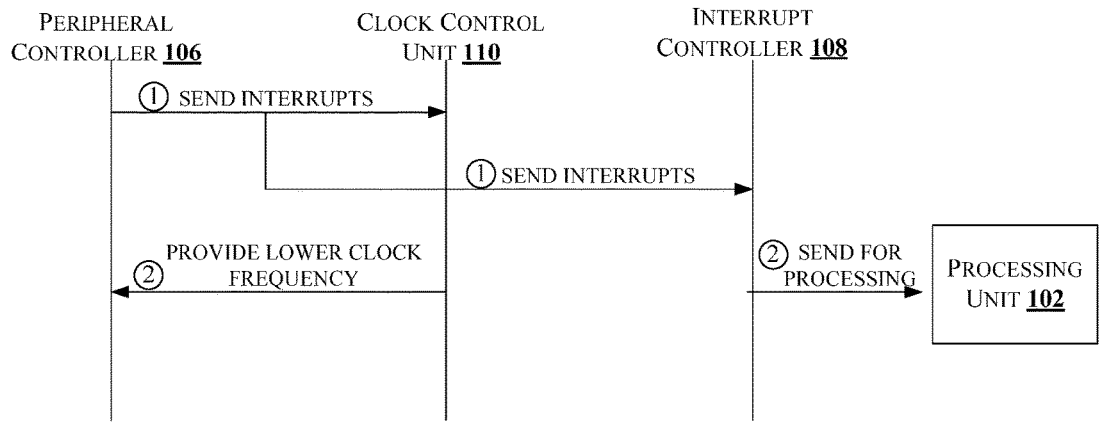
FIG. 2 illustrates a state diagram showing flow of interrupts and clock frequencies for optimizing power consumption of SoC in accordance with some embodiments of the present disclosure.

The process of reducing the normal operating clock frequency to the lower clock frequency by the clock control unit 110 is explained herein with the help of FIG. 2. FIG. 2 shows the flow between the peripheral controller 106, the clock control unit 110, the interrupt controller 108 and the processing unit 102 for optimizing the power consumption of the SoC 100. Consider, the peripheral controller 106 issues the one or more interrupt signal. The one or more interrupt signal reaches the processing unit 102 for processing the one or more interrupts through the interrupt controller 108 as shown as flows 1 and 2 (towards the processing unit 102). Simultaneously, the one or more interrupts issued by the peripheral controllers 106 is received by the clock control unit 110 from the one or more peripheral controllers 106 only as shown in flow 1. Considering, the kind of interrupt signal issued by the peripheral controller 106 is the precautionary interrupt signal which needs intervention of the processing unit 102. The precautionary interrupt like "ALMOST FULL" may be received from the peripheral controller 106 which is indicating that the FIFO inside the peripheral/Processing IP is getting full which needs the intervention of the processing unit 102. Upon detecting the precautionary interrupt signal, the clock control unit 110 reduces the clock frequency of the peripheral controller 106 to the lower clock frequency than the normal operating clock frequency. Thus data movement into the peripheral controller 106 is controlled which avoids FIFO FULL or OVERFLOW interrupt generation. Since clock frequency is reduced, the dynamic power consumed by the fanout of the clock control unit 110 is saved. Also, in such a way, load on the processing unit 102 is reduced.

Considering, the peripheral controller 106 issues the low priority interrupt signal, for example, data transfer completion from a slow peripheral like the I2C, which is processed by the processing unit 102 very later after completing the processing of all other high priority interrupts and high priority tasks. During such a stage, the clock frequency to the peripheral controller 106 can be reduced. Hence during the wait time where peripheral controller 106 is waiting for the intervention of the processing unit 102 to process the low priority interrupt signal, clock frequency is reduced which reduces the dynamic power consumption without impacting the performance.

Figure 3:
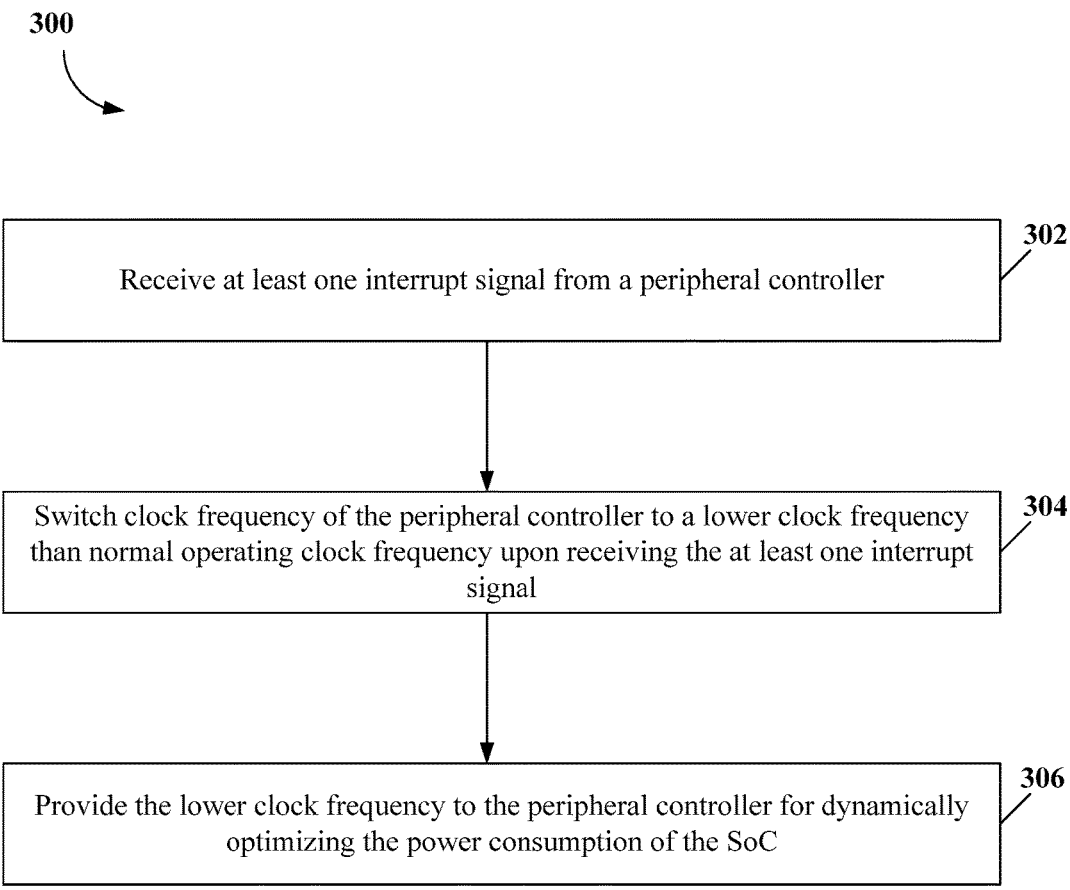
FIG. 3 shows a flowchart illustrating a method for optimizing power consumption of SoC by reducing clock frequencies to peripheral controllers in wait state in accordance with some embodiments of the present disclosure.

FIG. 3 shows a flowchart illustrating a method 300 for optimizing the power consumption of the SoC 100 in accordance with some embodiments of the present disclosure.

As illustrated in FIG. 3, the method 300 comprises one or more blocks for optimizing the power consumption of the SoC 100. The method 300 may be described in the general context of controller/processor executable instructions.

The order in which the method 300 is described is not intended to be construed as a limitation, and any number of the described method blocks can be combined in any order to implement the method. Additionally, individual blocks may be deleted from the methods without departing from the scope of the subject matter described herein.

At block 302, the one or more interrupt signal is received from the one or more peripheral controller 106 by the clock control unit 110. In an embodiment, the one or more interrupt signal is generated by the peripheral controller to the processing unit of the SoC 100 for processing. In an embodiment, the one or more interrupt signal reaches the processing unit 102 through the interrupt controller 108.

At block 304, the clock control unit 110 switches the clock frequency of the one or more corresponding peripheral controller 106 to the lower clock frequency than the normal operating clock frequency upon receiving the one or more interrupt signal. In an embodiment, the clock control unit 110 switches the clock frequency to the lower clock frequency upon receiving the precautionary interrupt signal and/or the low priority interrupt signal.

At block 306, the clock control unit 110 provides the lower clock frequency to the peripheral controller 106 depending on the main control logic and/or the interface control logic for dynamically optimizing the power consumption of the SoC 100.

Advantages of the embodiment of the present disclosure are illustrated herein.

Embodiments of the present disclosure reduce CPU load time and SoC power by optimizing the power consumption.

Embodiments of the present disclosure modify clock frequency to the peripheral controller which doesn't hamper the overall performance of the SoC.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself The illustrated operations of FIG. 3 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the disclosure of the embodiments of the invention is intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

REFERRAL NUMERALS

| Reference Number | Description |
|---|---|
| 100 | System-on-Chip (SoC) |
| 102 | Processing Unit |
| 104 | Bus Hierarchy |
| 106a, . . . , 106n | Peripheral Controller |
| 108 | Interrupt Controller |
| 110 | Clock Control Unit |
| 112 | Memory |

What is claimed is:

1. A method for dynamically optimizing power consumption in a System-on-Chip (SoC), the method comprising:
   receiving, by a clock control unit of the SoC, at least one interrupt signal from a peripheral controller wherein at least one interrupt corresponding to the at least one interrupt signal is waiting to be serviced by a CPU of the SoC;
   detecting, by the clock control unit, the at least one interrupt signal from a peripheral controller as at least one of a precautionary interrupt signal and a low priority interrupt;
   switching, by the clock control unit, clock frequency of the peripheral controller to a lower clock frequency than a normal operating clock frequency upon the detection, during at least one of a wait period or a data rate adjustment associated with the at least one interrupt signal; and
   providing, by the clock control unit, the lower clock frequency than the normal operating clock frequency to the peripheral controller until the at least one interrupt is serviced by the CPU, for dynamically optimizing the power consumption of the SoC.

2. The method as claimed in claim 1, wherein the peripheral controller is internally configured to the SoC.

3. The method as claimed in claim 1, wherein the at least one interrupt signal is generated by the peripheral controller to a processing unit of the SoC for processing the at least one interrupt signal.

4. The method as claimed in claim 1, wherein the clock frequency is provided to the peripheral controller depending on at least one of main control logic and interface control logic.

5. A System-on-Chip (SoC) with dynamically optimizing power consumption, comprising:
   a processing unit;
   a memory communicatively coupled to the processing unit, wherein the memory stores processor-executable instructions, which, on execution, cause the processing unit to process at least one interrupt signal;
   one or more peripheral controllers, wherein the one or more peripheral controllers provide the at least one interrupt signal to the processing unit for processing the at least one interrupt signal; and
   a clock control unit configured to:
      receive the at least one interrupt signal from a peripheral controller of the one or more peripheral controllers wherein at least one interrupt corresponding to the at least one interrupt signal is waiting to be serviced by a CPU of the SoC:
      detect the at least one interrupt signal from a peripheral controller as at least one of a precautionary interrupt signal and a low priority interrupt;

switch clock frequency of the peripheral controller to a lower clock frequency than a normal operating clock frequency upon the detection, during at least one of a wait period or a data rate adjustment associated with the at least one interrupt signal; and provide the lower clock frequency than the normal operating clock frequency to the peripheral controller until the at least one interrupt is serviced by the CPU, for dynamically optimizing the power consumption of the SoC.

6. The SoC as claimed in claim 5 is configured with the peripheral controller.

7. The SoC as claimed in claim 5, wherein the clock frequency is provided to the peripheral controller depending on at least one of main control logic and interface control logic.

* * * * *